United States Patent
Weiss

Patent Number: 6,113,296
Date of Patent: Sep. 5, 2000

[54] VALVE ARRANGEMENT FOR CONTROLLING A FLOW OF FLUID BETWEEN TWO FLUID CHAMBERS AND WRITING IMPLEMENT PROVIDED THEREWITH

[76] Inventor: Oliver Weiss, Borkweg 45, D-90530 Wendelstein, Germany

[21] Appl. No.: 09/217,763

[22] Filed: Dec. 21, 1998

Related U.S. Application Data

[63] Continuation of application No. PCT/EP97/02935, Jun. 6, 1997.

[30] Foreign Application Priority Data

Jul. 3, 1996 [DE] Germany .............................. 196 26 755

[51] Int. Cl.[7] ...................................................... B43K 5/00
[52] U.S. Cl. ............................ 401/199; 401/264; 401/206
[58] Field of Search ..................................... 401/272, 273, 401/264, 199, 206, 235, 236, 151, 230

[56] References Cited

U.S. PATENT DOCUMENTS

| | | |
|---|---|---|
| 3,054,134 | 9/1962 | Meyerhoefer ............................ 401/206 |
| 4,549,879 | 10/1985 | Groshong et al. . |
| 4,620,648 | 11/1986 | Schwartzman ........................... 401/264 |
| 4,737,152 | 4/1988 | Alchas . |
| 5,250,034 | 10/1993 | Apling et al. . |

FOREIGN PATENT DOCUMENTS

| | | |
|---|---|---|
| 1360234 | 8/1964 | France . |
| 95/11283 | 4/1995 | WIPO . |

*Primary Examiner*—David J. Walczak
*Attorney, Agent, or Firm*—Ladas & Parry

[57] ABSTRACT

A valve arrangement for controlling the flow of fluid between a first and a second fluid chamber, wherein an elastomer material hose part (2) has an outer surface in contact with the first fluid chamber (5') and a lumen (6) of the hose part is connected to the second fluid chamber (9), one or a plurality of continuous slots (2) being provided in the wall of the hose part (2), which slots, in a non-deformed state of the hose part (2), are closed due to the inherent restoring force of the elastomer of the hose part and can be opened by deforming the hose part (2), is disposed on the hose part is an actuating part (10) by which the hose part (2) can be deformed to control the flow of fluid through the slots (11). The valve arrangement can be used in a writing implement.

9 Claims, 3 Drawing Sheets

VALVE ARRANGEMENT FOR CONTROLLING A FLOW OF FLUID BETWEEN TWO FLUID CHAMBERS AND WRITING IMPLEMENT PROVIDED THEREWITH

This application is a continuation of Ser. No. PCT/EP97/02935 filed Jun. 6, 1997.

DESCRIPTION

1. Field of the Invention

The invention concerns a valve arrangement for control of a fluid passage between a first and a second fluid chamber as well as a writing device equipped with it.

2. Background

Basically, there is currently a requirement for valves that are miniaturized and can be constructed in a simple manner, due to the miniaturization that is taking place in many technical fields, which [valve] can be utilized, among other things, for control purposes in micropneumatics and microhydraulics. Technologies relating to medicine and writing devices also require such valves.

SUMMARY OF THE INVENTION

In order to solve this problem, the invention concerns a valve device of the above type with the following features:

a hose part of elastomer material, whose wall outer side stands in contact with a first fluid chamber and whose inside space or lumen is joined with a second fluid chamber, one or more penetrating slots in the wall of the hose part, which are to be closed in the underformed state of the house part, due to the restoring force of the elastomer material inherent in the material, and which can be opened by deformation of the hose part, and an actuating part on the hose part, by means of which, the hose part can be deformed in order to control the flow of fluid through the slot.

It is clear from the above combination of features that a valve for the throughput control of gases and liquids that is to be actuated mechanically forms the basis for the subject of the invention. The two mentioned fluid chambers may therefore be two closed volumes or also a supply space and its surroundings or atmosphere, as will be explained in the following in more detail on the basis of an example.

The hose part advantageously comprises silicone material. This reduces the production expense for the valve arrangement according to the invention, since silicone tubing can already be obtained in many dimensions and qualities as a commercially mass-produced application for the valve. Silicone is compatible with skin and tolerated by the body.

Most preferably, the actuating part is formed as a tube piece sitting in the lumen of the hose part, and ending in front of its slot region. This construction assures small actuating forces and a perfect discharge of the fluid passing through the slot that has been opened by deformation, from the first to the second fluid chamber.

The arrangement and the precise configuration of the slots in the hose part can be established each time oriented toward the application. It must only be assured that the slots are closed in the undeformed state of the hose part. These must thus involve fine cuts and not coarse openings in the wall of the hosing part.

In order to obtain a response characteristic of the valve that is independent of the direction of deformation, it may be preferred to provide one or more peripherally-running series of slots in the hose part.

By a fluid-tight mounting of the hose part each time in front of its two ends, a clean attachment of the hose part as well as a separation between the two fluid chambers is obtained.

In summary, the following can be named as advantages of the valve arrangement according to the invention: Its corrosion resistance and very high chemical resistance, particularly against acids and bases—no metallic parts need to be used; its very small space requirement; and the small actuating forces. Further, the valve arrangement can be used in a broad temperature range. Not lastly, only those materials are used, which exclude a buildup of sparks, so that the valve arrangement can be utilized also in an environment that is at risk of explosion.

As a preferred application of the valve arrangement according to the invention, application in a writing device is provided for the regulation of the flow of ink between an ink reservoir of the writing device and its writing tip.

BRIEF DESCRIPTION OF THE DRAWINGS

Relative to the claimed further development of the writing device with such a valve arrangement, in order to avoid unnecessary repetition, refer to the following description, in which the valve arrangement itself and a writing device provided therewith, including additional features, characteristics and advantages will be explained in detail on the basis of the attached drawings.

Therein.

DETAILED DESCRIPTION

Figure 1:
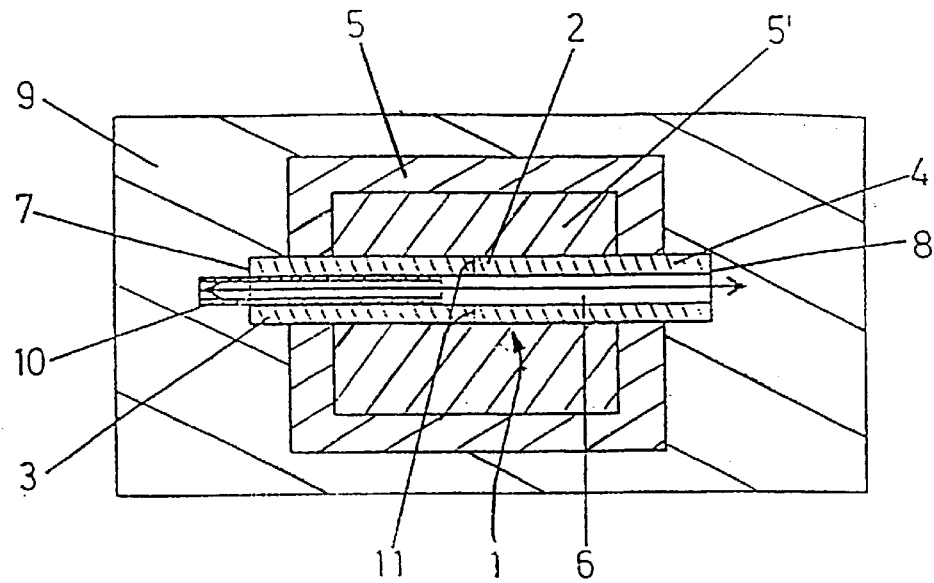
FIGS. 1 and 2 show schematic views of the valve arrangement in closed and open position.
Figure 2:
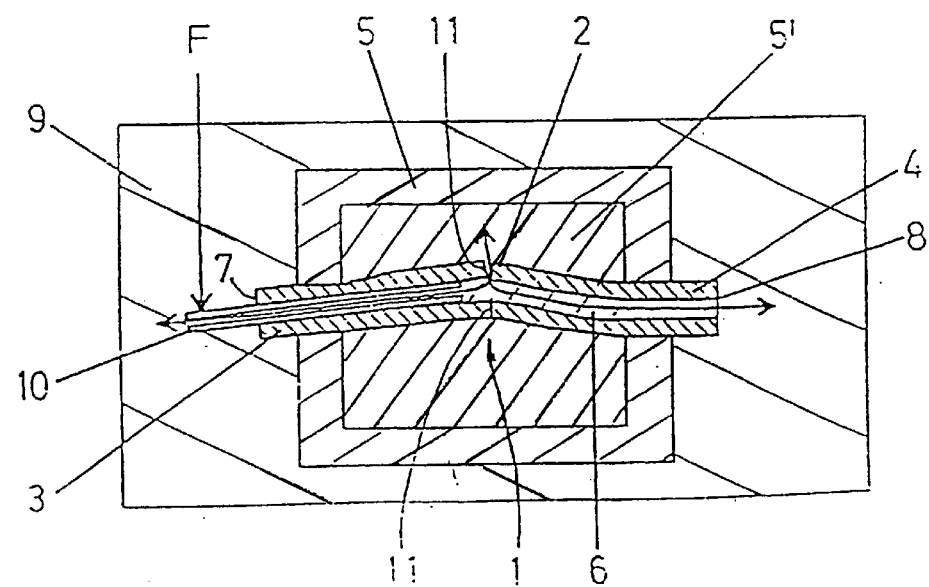

Valve arrangement 1 according to the invention is shown in highly schematic form in FIGS. 1 and 2. Its core piece is a short hose part 2 of silicone material, which is mounted in front of its two open ends 3, 4 in a fluid-tight manner in a housing part 5. Housing part 5 belongs to a first fluid chamber 5', in which a fluid, e.g., a liquid stands. Hose part 2 on the outer side of its wall is thus surrounded by the liquid in first fluid space 5' between the mounting places at the two open ends. Lumen 6 of hose part 2, by its two openings 7, 8, opens up into a second fluid chamber, which is designated in its entirety as 9 in FIGS. 1 and 2 and is indicated by the broad-hatched surface. A tube piece 10 as an actuating part is inserted into lumen 6 of hose part 2 through one opening 7, and this terminates just before the region of slot 11 in hose part 2.

Figure 3:
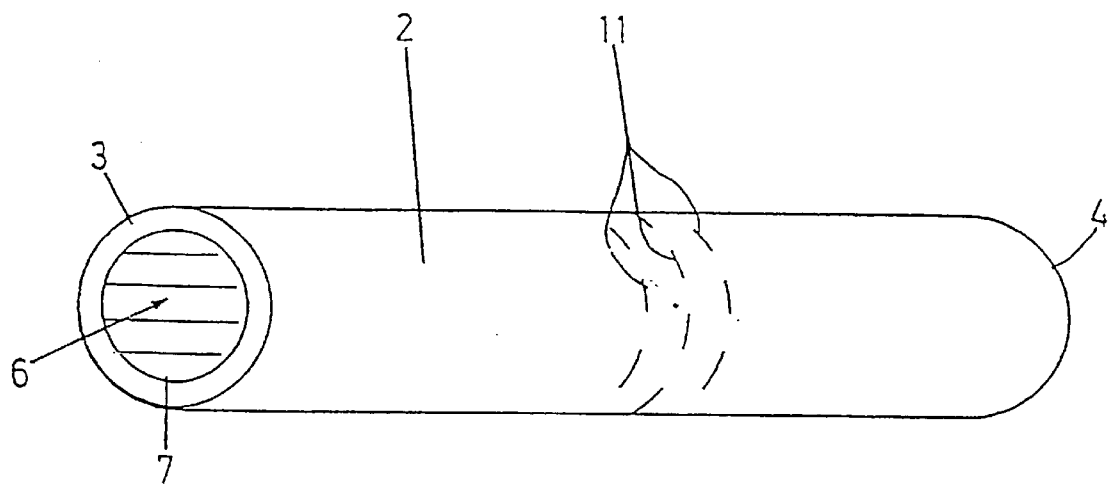
FIGS. 3 and 4 show an enlarged representation of the hose part of FIG. 1 in the unstressed and deformed state.
Figure 4:
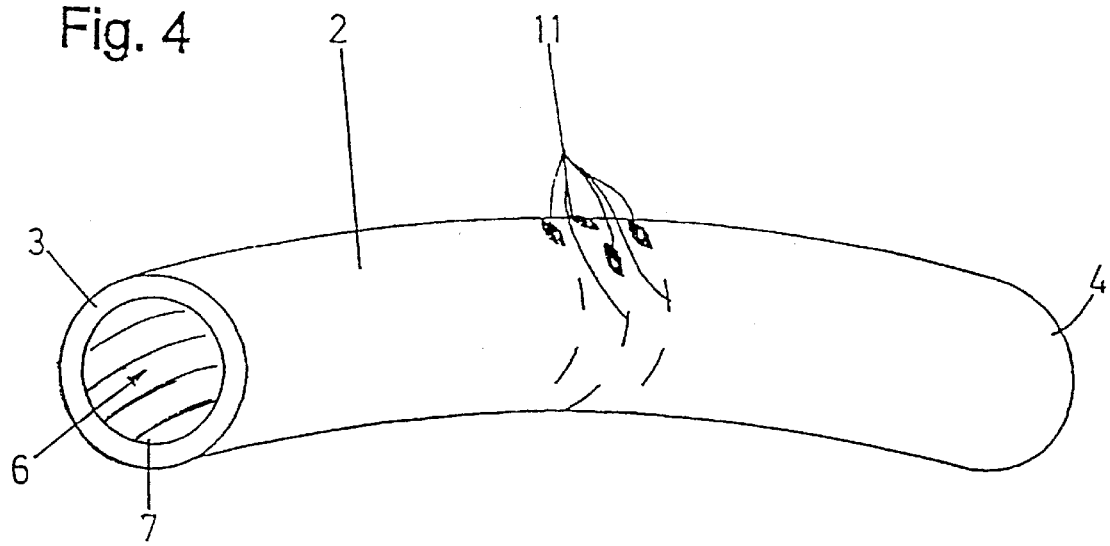

An example of the shaping and configuration of slot 11 is shown in FIGS. 3 and 4. Three rows of peripherally running slots 11 are provided approximately in the middle with reference to the length of hose part 2. Slots 11 are microfine cuts, which run through the wall of the hose part.

Valve arrangement 1 is shown in closed position in FIG. 1. Slots 11 are closed due to the restoring force of its silicone elastomer material inherent in the material residing in hose part 2, so that fluid found in housing part 5 (first fluid chamber 5=) with slight overpressure cannot enter through slot 11 into lumen 6 of hose part 2.

Upon action of a force F onto tube piece 10 projecting from hose part 2, hose part 2 is deflected and deformed, as can be seen in FIG. 2. Slots 11, which lie on the extended side of hose part 2, are opened by this deformation and fluid or gas can pass from housing part 5 (first fluid chamber 5') through the slots into lumen 6 of hose part 2 and from there through openings 7,8, into second fluid chamber 9. The opening of slots 11 is exaggerated in FIG. 4, but presented so that it is obvious.

If force F no longer acts, then hose part 2 again becomes straight and slots 11 are closed all around. The fluid connection between first fluid chamber 5' and second fluid chamber 9 is thus again interrupted.

Figure 5:
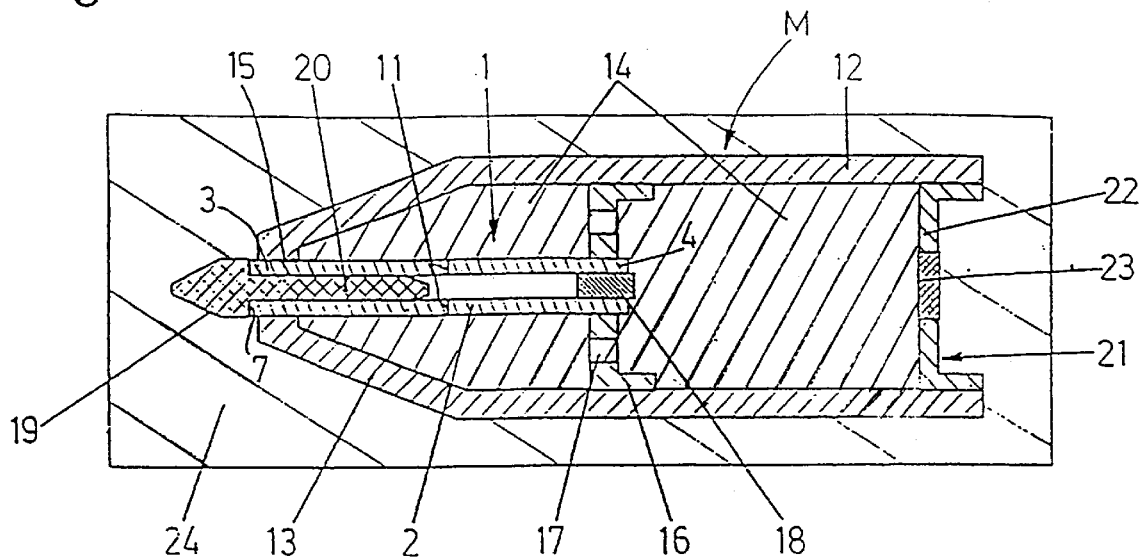
FIGS. 5 and 6 show schematic longitudinal sections through a marking pen with a closed and opened valve arrangement.
Figure 6:
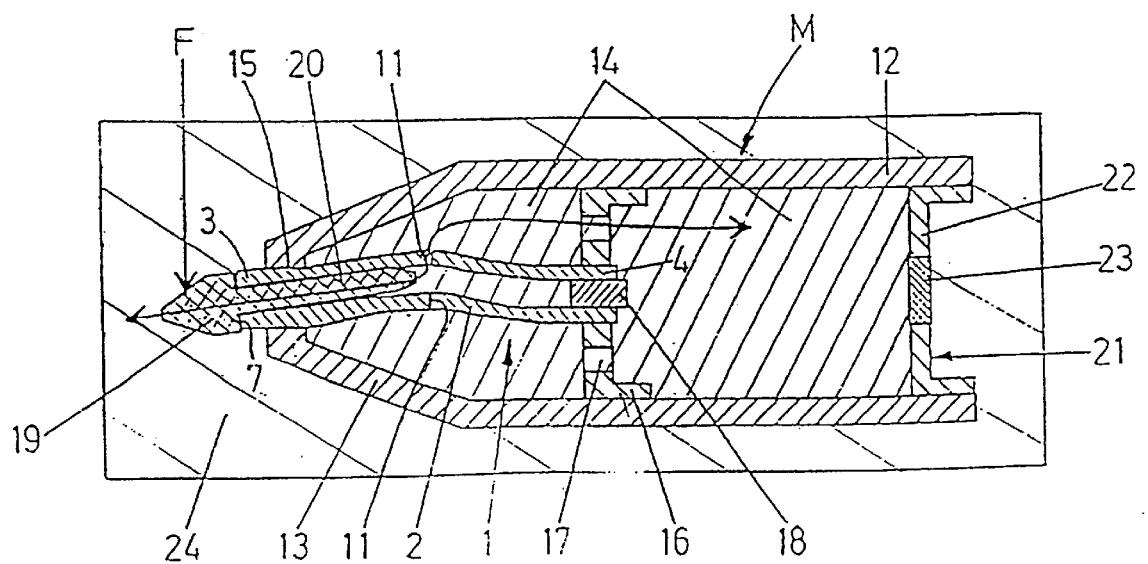

A practical example of the application of the valve arrangement presented in FIGS. 1 through 4 is shown in FIGS. 5 and 6. This involves a marking pen M shown schematically in section, which has a conventional cylindrical or flattened tube-shaped apparatus housing 12 with conically running housing tip 13. Housing 12 surrounds a reservoir 14 for the writing fluid of the marking pen.

An opening 15 is provided in housing tip 13, in which one end 7 of hose part 2 is mounted by its outer side in a fluid-tight sealing manner. Hose part 2 arranged coaxially to the longitudinal axis of apparatus housing 12 is further arranged by its other end 4 in an apparatus holding element 16 in housing 12, which has passage openings 17 for the writing fluid. Opening 8 of hose part 2 lying at end 4 is tightly sealed by a plug 18 in the form of a silicone cord piece. Writing tip 19 of marking pen M is inserted by its shaft 20 into opening 7 lying opposite, which lies outside apparatus housing 12. Writing tip 19 itself forms the actuating part for valve arrangement 1, whereby its shaft 20 reaches further up to just in front of slots 11 in hose part 2. Writing tip 19 with shaft 20 is further produced from fiber material, as is usual for marking pens M for transport of writing fluid based on capillary action.

Opening 21 of the apparatus housing turned away from housing tip 13 is moreover closed by a cap 22, in which a pressure equilibration element 23 in the form of a hydrophobic, semipermeable membrane is inserted. The latter is welded ultrasonically with cap 22.

The control of the flow of ink in marking pen M will be explained on the basis of FIG. 6:

If marking pen M is placed on a sheet of paper 24, as is indicated very schematically in FIG. 6, and then force F is introduced onto writing tip 19, hose part 2 will deflect from shaft 20 of writing tip 19 and deform. In this way, slots 11 in hose part 2 open, so that the liquid present in reservoir 14 (first fluid chamber) can enter into lumen 6 of hose part 2 and will be transported via capillary forces into writing tip 19 onto the sheet of paper 24. According to the above terminology, the latter forms practically the second fluid chamber. As soon as marking pen M is removed from the paper and force F is removed, hose part 2 again becomes straight and the flow of ink from reservoir 14 to writing tip 19 is interrupted.

Finally, the advantages of the writing device according to the invention, as have been described above, are summed up as follows:

The regulation of the flow of ink is conducted by an uncomplicated, cost-favorable valve system.

The functional principle is applicable to many types of writing pastes and liquids, as well as for cosmetic fluids.

The tank content of the writing device is determined only by the housing size and is thus arbitrarily selected within certain limits.

More than 90% of the writing fluid can be utilized. From this results an essentially higher productivity with the same filling quantity in comparison to fiber storage systems.

The writing behavior is independent of the residual tank content.

The writing device is secure against shock, i.e., when dropped, there is no sudden appearance of writing fluid and associated blotches.

The writing device can be configured in a refillable manner.

The writing tip can be arbitrarily shaped and can be designed in an exchangeable manner, since it is inserted only into the hose part.

The writing device is optimally recyclable, since the individual parts are easy to dismantle and separate, based on the simple construction.

What is claimed is:

1. Valve arrangement for control of a fluid through-flow between a first and a second fluid space comprising:

a flexible tubing piece (2) of elastomer material, having deformed and undeformed states, said tubing piece having an outer wall side adapted to be in contact with the first fluid space (5', 14) and a lumen (6) adapted to be joined with the second fluid space (9,24), at least one through slot (11) in the wall of the flexible tubing piece (22) which is closed when the flexible tubing piece (2) is in the undeformed state due to inherent restoring force of the elastomer material and which can be opened by deformation of said flexible tubing piece (2), and an actuation part (10, 19) on said tubing piece (2) by which the tubing piece (2) can be deformed for control of fluid flow through said at least one slot (11), wherein the actuation part is formed as a tube piece (10) disposed in the lumen (6) of the flexible tubing piece (2) and ending in front of said at least one slot (11).

2. Valve arrangement according to claim 1, wherein the flexible tubing piece (2) is comprised of silicone material.

3. Valve arrangement for control of a fluid through-flow between a first and a second fluid space comprising:

a flexible tubing piece (2) of elastomer material, having deformed and undeformed states, said tubing piece having an outer wall side adapted to be in contact with the first fluid space (5', 14) and a lumen (6) adapted to be joined with the second fluid space (9,24), at least one through slot (11) in the wall of the flexible tubing piece (22) which is closed when the flexible tubing piece (2) is in the undeformed state due to inherent restoring force of the elastomer material and which can be opened by deformation of said flexible tubing piece (2), and an actuation part (10, 19) on said tubing piece (2) by which the tubing piece (2) can be deformed for control of fluid flow through said at least one slot (11), wherein a plurality of said slots are provided extending in peripheral rows in said flexible tubing piece (2).

4. Valve arrangement for control of a fluid through-flow between a first and a second fluid space comprising:

a flexible tubing piece (2) of elastomer material, having deformed and undeformed states, said tubing piece having an outer wall side adapted to be in contact with the first fluid space (5', 14) and a lumen (6) adapted to be joined with the second fluid space (9,24), at least one through slot (11) in the wall of the flexible tubing piece (22) which is closed when the flexible tubing piece (2) is in the undeformed state due to inherent restoring force of the elastomer material and which can be opened by deformation of said flexible tubing piece (2), and an actuation part (10, 19) on said tubing piece (2) by which the tubing piece (2) can be deformed for control of fluid flow through said at least one slot (11), wherein said flexible tubing piece (2) is mounted in a fluid-tight manner in front of its two ends (3,4).

5. Recording device with a valve arrangement according to claim 1 for regulating the flow of ink between an ink reservoir (14) and a recording tip (19).

6. Recording device according to claim 5, wherein said flexible tubing piece (2) of the valve arrangement (1) is mounted in a housing (12) in such a way that one end (3) of said flexible tubing piece (2) opens outwardly from said housing (12), said one end of the flexible tubing place having a mouth opening (7) provided with a recording tip (19), a second end (4) of said tubing piece (2) being closed, said flexible tubing piece (2) having a part between said ends which is provided with said at least one slot (11) which lies inside said housing (12) and connects on the outer wall side with the ink reservoir (14) of the recording device.

7. Recording device according to claim 6 wherein the recording tip (19) is provided with a shaft (20) protruding into the lumen (6) of the flexible tubing piece (2).

8. Recording device according to claim 7 wherein the shaft (20) terminates in the direct vicinity of said at least one slot (11) of the valve arrangement (1).

9. Recording device according to claim 5, further wherein an end of the flexible tubing piece (2) remote from the recording tip (19) is attached in a mounting element (16) inside the housing.

* * * * *